(12) United States Patent
Solorio et al.

(10) Patent No.: US 11,992,577 B2
(45) Date of Patent: May 28, 2024

(54) ADHESIVE FOR SURGICAL STAPLE LINE REINFORCEMENT

(71) Applicant: Cook Biotech Incorporated, West Lafayette, IN (US)

(72) Inventors: Loran Solorio, West Lafayette, IN (US); Steven Cohen, West Lafayette, IN (US); Benjamin Patrick Kline, Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 177 days.

(21) Appl. No.: 17/443,470

(22) Filed: Jul. 27, 2021

(65) Prior Publication Data

US 2022/0023489 A1    Jan. 27, 2022

Related U.S. Application Data

(60) Provisional application No. 63/057,027, filed on Jul. 27, 2020.

(51) Int. Cl.
| | |
|---|---|
| *A61L 24/10* | (2006.01) |
| *A61L 24/00* | (2006.01) |
| *C08L 1/28* | (2006.01) |
| *C08L 5/08* | (2006.01) |

(52) U.S. Cl.
CPC .......... *A61L 24/102* (2013.01); *A61L 24/001* (2013.01); *A61L 24/108* (2013.01); *C08L 1/286* (2013.01); *C08L 5/08* (2013.01); *A61L 2300/414* (2013.01)

(58) Field of Classification Search
CPC ...... A61L 24/102; A61L 24/001; A61L 24/08; A61L 2300/414; C08L 1/286; C08L 5/08
See application file for complete search history.

(56) References Cited

U.S. PATENT DOCUMENTS

| | | | |
|---|---|---|---|
| 9,150,318 B1 * | 10/2015 | Sun | A61L 2/007 |
| 2008/0200949 A1 | 8/2008 | Hiles et al. | |
| 2009/0222994 A1 * | 9/2009 | Wood | A61H 15/0092 |
| | | | 5/652 |
| 2020/0100943 A1 * | 4/2020 | Leung | A61B 17/08 |

FOREIGN PATENT DOCUMENTS

| | | |
|---|---|---|
| JP | S63-18484 | 1/1988 |
| JP | S63-189484 A | 8/1988 |

OTHER PUBLICATIONS

English abstract for JP S63-189484 A obtained from Google Patents on Aug. 4, 2023.

\* cited by examiner

*Primary Examiner* — Shirley V Gembeh
(74) *Attorney, Agent, or Firm* — Woodard Emhardt Henry Reeves & Wagner

(57) ABSTRACT

The present disclosure provides medical products including an adhesive containing a carboxyalkyl cellulose and sorbitol. Such medical products can find use as a bolster material for use in conjunction with a surgical fastening device such as a stapler. Such adhesives may include advantageous properties such as the ability to retain tack while stored under a peelable cover. Related methods of manufacture and use are also described.

14 Claims, 3 Drawing Sheets

Stapler Adhesion Test Results During Aging

ADHESIVE FOR SURGICAL STAPLE LINE REINFORCEMENT

CROSS REFERENCE TO RELATED APPLICATION

This application claims the benefit of Provisional Patent Application Ser. No. 63/057,027 filed Jul. 27, 2020.

BACKGROUND

The present disclosure resides generally in the field of medical adhesives and in particular aspects to materials and devices including such adhesives for use in a variety of medical applications.

As further background, medical adhesives have been utilized in medical applications either alone or in conjunction with medical materials. When included on a medical material, the material can be applied to a patient as a tissue graft, or can be further included as part of a medical device, e.g., a surgical stapler.

Medical adhesives have been used on both synthetic and biological materials. With respect to biological materials, a variety of extracellular matrix (ECM) materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902,508, 4,956,178, 5,281,422, 5,554,389, 6,099,567 and 6,206,931. In addition, Cook Biotech Incorporated, West Lafayette, Ind., currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379,710. As well, ECM materials derived from amnion (see e.g. U.S. Pat. Nos. 4,361,552 and 6,576,618) and from renal capsule membrane (see International PCT Patent Application No. WO 03/002165 published Jan. 9, 2003) have been proposed for medical and/or cell culture applications. Any adhesive included on a medical material must be compatible with both the material and any tissue to which it may be applied.

In certain applications, medical materials have been used in conjunction with surgical stapler devices as a bolster material. Such devices are designed to seal or simultaneously cut and seal an extended segment of tissue in a patient with staples, and a bolster material can be used to further secure the staples. The use of a bolster material finds particular use when the patient's tissue to be sealed is too fragile to securely hold the staples in place. For example, in the case of lung tissue, and in particular diseased lung tissue, the tissue to be stapled is fragile and, in extreme cases, will easily tear through unprotected staple lines. With the growing use of surgical staplers in operations on diseased lung tissues such as bullectomies and volume reduction procedures, it has become increasingly important to take measures to protect fragile tissue from tissue tears due to surgical staples or surgical stapling procedures. In many cases, as a preliminary step, the bolster material is in some manner applied to the arms of the surgical stapler, e.g. with portions applied to each arm, and the stapler thereafter used to secure tissue of the patient. In such applications, it is desirable to apply the bolster material in a manner that it is easily removable from the arms of the surgical stapler, such as after the staples have been forced through the material. Adhesives have been used for this purpose.

Prior medical adhesive formulations are indicated for application to the medical material (e.g. bolster material) immediately prior to adhesion of the material to a surgical stapling device. Such a requirement introduced additional manipulation within the operating procedure and resulted in uneven application of the adhesive and poor performance.

With respect to the above, it is apparent that a need remains for improved and/or alternative medical adhesives that can be used in a wide variety of medical applications. The present invention provides such medical adhesives, as well as medical products and methods related thereto.

SUMMARY

In one aspect, the present invention provides a medical product comprising a medical graft material and including an adhesive on at least a portion of a surface of the medical product. In accordance with some forms, the adhesive comprises a carboxyalkyl cellulose and sorbitol. In certain embodiments, the carboxyalkyl cellulose comprises carboxymethyl cellulose. In some forms, the adhesive further comprises a sulfated glycosaminoglycan, maltitol, and/or a salt. In certain embodiments, the sulfated glycosaminoglycan comprises chondroitin sulfate. In certain embodiments, the salt comprises sodium chloride. In some forms, the medical product further comprises a peelable protective cover over the adhesive. In certain embodiments, the disclosure provides for a medical product contained within a sterile package, preferably a package which is configured contain the medical product within an inner space and to maintain the inner space at a humidity level of 50-65% relative humidity. In accordance with some forms, the medical graft material comprises a biological material, for example an extracellular matrix material. In some forms, the medical graft material comprises a bolster material configured for application to an arm of a surgical fastening device. The present disclosure also provides for a medical product wherein the adhesive is present on a portion of a surface of the medical graft material, wherein the coated portion comprises at least 80% of the surface.

The present disclosure provides a medical product comprising a layer of dried collagenous extracellular matrix material, the layer having a surface and a coated portion of the surface, and an adhesive coating the surface within the coated portion, the adhesive comprising a carboxyalkyl cellulose and sorbitol. In certain embodiments, the carboxyalkyl cellulose comprises carboxymethyl cellulose. In some forms, the adhesive further comprises a sulfated glycosaminoglycan, maltitol, and/or a salt. In certain embodiments, the sulfated glycosaminoglycan comprises chondroitin sulfate. In certain embodiments, the salt comprises sodium chloride. In some forms, the medical product further comprises a peelable protective cover over the adhesive. In certain embodiments, the disclosure provides for a medical product contained within a sterile package, preferably a package which is configured to contain the medical product within an inner space, the package configured to maintain the inner space at a humidity level of 50-65% relative humidity. In some forms, the medical graft material comprises a bolster material configured for application to an arm of a surgical fastening device. The present disclosure also provides for a medical product wherein the coated portion comprises at least 80% of the surface.

In another embodiment, the disclosure provides a method for preparing a medical product, the method comprising providing a medical material as a first layer, applying an adhesive to at least a portion of a surface of the medical material, the adhesive comprising a carboxyalkyl cellulose and sorbitol, and applying a peelable protective cover to the adhesive, the peelable protective cover peelable to expose the adhesive on the medical material. In certain embodiments, the carboxyalkyl cellulose comprises carboxymethyl cellulose. In some forms, the adhesive further comprises a sulfated glycosaminoglycan, maltitol, and/or a salt. In certain embodiments, the sulfated glycosaminoglycan comprises chondroitin sulfate. In certain embodiments, the salt comprises sodium chloride. In some forms, the medical product further comprises a peelable protective cover over the adhesive. In accordance with some forms, the medical graft material comprises a biological material, for example an extracellular matrix material. In some forms, the medical graft material comprises a bolster material configured for application to an arm of a surgical fastening device. The present disclosure also provides for a medical product wherein the adhesive is present on a portion of a surface of the medical graft material, wherein the coated portion comprises at least 80% of the surface.

In a further embodiment, the disclosure provides a bolster material configured for application to an arm of a surgical fastening device, the bolster material comprising an adhesive coating on at least a portion of a surface of the bolster material, wherein the adhesive coating comprises a carboxyalkyl cellulose and sorbitol. In certain embodiments, the carboxyalkyl cellulose comprises carboxymethyl cellulose. In some forms, the adhesive further comprises a sulfated glycosaminoglycan, maltitol, and/or a salt. In certain embodiments, the sulfated glycosaminoglycan comprises chondroitin sulfate. In certain embodiments, the salt comprises sodium chloride. In some forms, the bolster material further comprises a peelable protective cover over the adhesive. In certain embodiments the disclosure provides for a bolster material contained within a sterile package, preferably a package which is configured to contain the bolster material within an inner space having a humidity level of 50-65% relative humidity. In accordance with some forms, the bolster material comprises a biological material, for example an extracellular matrix material. The present disclosure also provides for a bolster material wherein the adhesive is present on at least 80% of the surface of the bolster material.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
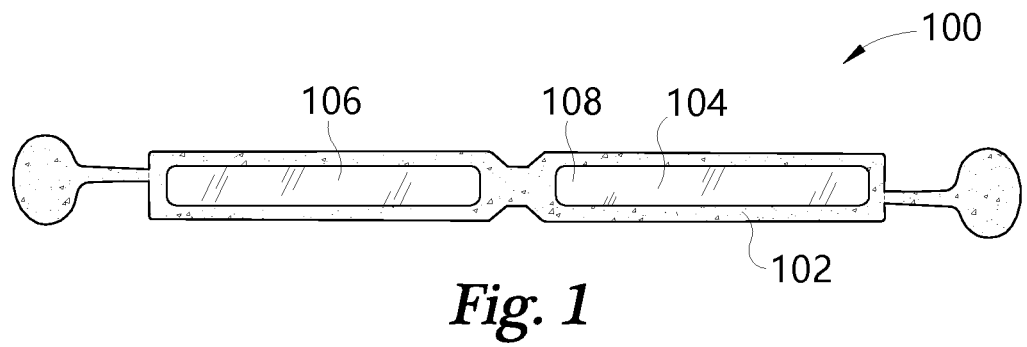
FIG. 1 is a top down view of one embodiment of a medical product as provided by the present disclosure.

For the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one skilled in the art to which the invention relates. One embodiment of the disclosure is shown in great detail, although it will be apparent to those skilled in the relevant art that some features that are not relevant to the present disclosure may not be shown for the sake of clarity.

As disclosed herein, in certain aspects, the present disclosure provides medical products useful in a wide variety of applications. Such medical products include an advantageous adhesive comprising a carboxyalkyl cellulose, and sorbitol. Desirable adhesives retain tack and performance characteristics for at least one month aging after application.

In certain embodiments, the present disclosure provides an adhesive comprising a carboxyalkyl cellulose and sorbitol. In accordance with some forms, the present disclosure provides an adhesive comprising carboxyalkyl cellulose, sorbitol, and one or more of the following: sulfated glycosaminoglycan(s), salt(s), additional sugar alcohols, and/or water. As used herein, carboxyalkyl cellulose refers to a cellulose derivative with carboxyalkyl groups bound to some of the hydroxyl groups of the glucopyranose monomers that make up the cellulose backbone. In some forms, the adhesive of the present disclosure comprises carboxymethyl cellulose, carboxyethyl cellulose, and/or carboxypropyl cellulose.

In certain embodiments, the present disclosure provides adhesive compositions comprising glycosaminoglycans (GAG), including sulfated glycosaminoglycans (sGAG). GAG molecules are long chains of negatively charged polysaccharides. GAGs are polar and thus attract water. As used herein the term glycosaminoglycan may encompass one or more of the following: heparin, heparin sulfate, chondroitin sulfate, dermatan sulfate, keratin sulfate, and/or hyaluronic acid.

In some forms, the present disclosure provides adhesive compositions comprising one or more sugar alcohols. As used herein, sugar alcohol refers to sugar derived compounds containing a hydroxyl group attached to each carbon atom. Exemplary sugar alcohols that may be used in the adhesive formulations disclosed herein include: ethylene glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and/or polyglycitol. Certain preferred embodiments comprise sorbitol in addition to one or more additional sugar alcohols.

In certain embodiments, the present disclosure provides adhesive compositions comprising one or more crystallization inhibiting salts. As used herein, the term "crystallization inhibiting salts" may refer to any salt suitable for inhibiting crystallization of the sugar alcohol or sugar alcohols in the formulation. The crystallization inhibiting salt may include organic and inorganic salts. Suitable candidates for crystallization inhibiting salts include but are not limited to calcium chloride, calcium sulfate, magnesium chloride, sodium chloride, sodium acetate, sodium citrate, and/or sodium phosphate. Sodium salts such as sodium chloride, sodium acetate, sodium citrate, and/or sodium phosphate are particularly preferred.

As disclosed herein, in certain aspects the present disclosure provides medical adhesive compositions comprising a carboxyalkyl cellulose. In accordance with some forms, the carboxyalkyl cellulose is water-soluble. Suitable carboxyalkyl cellulose may include the free acid form or a salt thereof. In certain preferred embodiments, the carboxyalkyl cellulose is carboxymethyl cellulose, preferably sodium carboxymethyl cellulose. Carboxymethyl cellulose comprises long chain polymers derived from cellulose. Properties of the carboxymethyl cellulose vary with the average number of carboxymethyl groups substitutes per anhydroglucose unit in each cellulose molecule. This carboxy group substitution characteristic is generally referred to as the "degree of substitution," with the maximum degree of substitution possible designated as 3.0, because there are a maximum of three reactive hydroxyl groups in each anhydroglucose unit. In certain embodiments, the carboxymethyl cellulose has a degree of substitution of 0.4 to 1.2, preferably 0.65 to 0.85. In certain embodiments, the carboxymethyl cellulose has a viscosity of 10 to 1,000 cP (2% solution at 25 degrees Celsius), preferably 20 to 100 cP (2% solution at 25 degrees Celsius), and even more preferably 30 to 45 cP (2% solution at 25 degrees Celsius).

In accordance with some forms, medical products of the present disclosure may include a peelable protective cover over the adhesive coating. Such a peelable protective cover finds use, for instance, to protect the adhesive coating prior to its application to tissue or device. In particular, a protective cover can be included where a medical product is contained within a sterile package prior to use. A protective coating can be made of any suitable material and is preferably made of a non-stick material, such as Tyvek®. Such materials can stick to the adhesive coating, but are generally non-adhesive towards other surfaces. In this respect, a non-adhesive protective cover will not stick to the walls of a sterile package when the medical product is stored for any period of time. Just prior to use, the protective cover can be removed, and the medical product can be applied to a desired tissue or device.

In preferred embodiments, medical products of the disclosure are bolster materials that can be used in conjunction with a surgical fastening device, such as a surgical stapler. In such embodiments, it will be understood that a medical product of the disclosure may be used in conjunction with a variety of surgical fastening devices that insert fasteners of various designs, including for example one-part and multiple (e.g. two) part staples, tacks, or other penetrating fasteners where bolstering may provide a benefit. Suitable surgical fastening devices include those described in, for instance, U.S. patent application Ser. No. 11/060,078, published Jan. 5, 2006 as United States Patent Application Publication No. 20060004407.

As disclosed herein, the present disclosure provides an adhesive coating on at least one surface of a medical graft material. The adhesive coating may be configured in any suitable way to provide tack to the surface of the medical graft material. In accordance with some forms, the adhesive coating is applied in a generally homogenous layer covering at least 50% of the surface area of the coated surface. In certain preferred embodiments, the coated portion comprises at least 80% of the medical graft material surface, even more preferably at least 90% of the medical graft material surface.

Medical products of the invention can be used to treat a variety of tissue defects including the repair or reconstruction of nervous tissue, skin, cardiovascular tissue (including vascular tissue and cardiac tissue), pericardial tissue, muscle tissue, ocular tissue, periodontal tissue, bone, connective tissue such as tendons or ligaments, and others. Preferably, a medical product of the invention can be used to treat structural tissue defects, including those involving uroepithelium (e.g., bladder, urethra, ureter), gastrointestinal mucosa (e.g., oropharynx, esophagus, stomach, intestine), respiratory epithelium (e.g., trachea, bronchus) and vasculature (e.g., artery, vein, lymphatics). Medical products of the invention can be used in hernia repair, such as epigastric, umbilical, incisional, hiatal, femoral, and inguinal hernia repair. A hernia is described as the protrusion of an organ through a tissue, which may occur anywhere in the body. When in the lower abdominal area, it often involves penetration of the intestine into or through the abdominal wall. The medical product of the invention can be applied to the site of a hernia, and can be used in conjunction with surgery, if deemed necessary, to treat a patient having a hernia.

Generally, when configured for tissue repair, the medical product of the invention is cut or otherwise configured to a desired size for its end use. The medical product is preferably sized larger than the tissue defect to which it is applied. Sizing the medical material in this way allows for easy attachment to the surrounding tissue.

Although the adhesive coating can be sufficient to secure the medical product in place, in certain instances, be advantageous to more securely attach the medical product to tissue. For example, once the medical product has been placed on, in, or around the defect, the medical product can be more securely attached to the surrounding tissue using any of several known suitable attachment means. Suitable attachment means include, for example, stapling, suturing, and the like. In many embodiments, the medical material will be more securely attached to the surrounding tissue by sutures.

The medical product of the invention can be in a dehydrated or hydrated state. Dehydration of a medical product of the invention can be achieved by any means known in the art. Preferably, dehydration is accomplished by lyophilization, drying in a vacuum, air drying, heated (e.g. oven) drying, or any combination of these. Typically, the medical product will be dehydrated when it is to be stored for a period of time. Any suitable solution can then be used to rehydrate the medical material prior to use. Preferably, the rehydration solution comprises water or buffered saline. In certain embodiments, hydrating the medical product will activate the adhesive such that it can adhere to tissue or a device. The above-described methods of dehydration and rehydration of the medical product allow for an effective shelf life and convenient packaging.

In certain embodiments, the medical product can be crosslinked. A medical product can be crosslinked once formed the medical material and adhesive can be crosslinked separately before the adhesive is applied to the material, or both. Increasing the amount (or number) of crosslinkages within the medical product or between two or more layers of the medical material can be used to enhance its strength. However, when a remodelable material is used, the introduction of crosslinkages within the material may also affect its resorbability or remodelability. Consequently, in certain embodiments, a remodelable ECM material used in a medical product will substantially retain its native level of crosslinking, or the amount of added crosslinkages within the medical material will be judiciously selected depending upon the desired treatment regime. In many cases, the medical material will exhibit remodelable properties such that the remodeling process occurs over the course of several days or several weeks. In certain preferred embodiments, the remodeling process occurs within a matter of about 5 days to about 12 weeks.

For use in the present invention, introduced crosslinking of the medical product may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When multiple layers of a medical material are used to form a laminate material, the layers of the laminate can be additionally crosslinked to bond multiple layers of medical material to one another. Thus, additional crosslinking may be added to individual layers prior to coupling to one another, during coupling to one another, and/or after coupling to one another.

The adhesive can be applied to at least a portion of a surface of a medical material by any suitable means. Suitable means include, for example, brushing, spraying, dipping, roll coating, etc. Alternatively, a dried adhesive film can be separately prepared, and then attached to the medical material, e.g. by partial wetting of one side and bonding of that side to the medical material, optionally followed by re-drying. Typically, a substantial portion of a surface of a medical material is coated with the adhesive. By "substantial portion" is meant that at least about 75% of a specified surface (e.g. one side or the other of a sheet in certain circumstances) of a medical material is coated with an adhesive. In embodiments involving the use of a surgical fastening device, means of attachment will be such that it increases the efficiency of attachment of the medical product to the arm surface, so long as the attachment is not so permanent as to deleteriously interfere with release of the bolster material after the surgical stapler has been fired or otherwise actuated to insert the staple or staples. The medical adhesives described herein may advantageously allow loading of a bolster material onto an uneven loading surface of a surgical stapling device. The adhesive can be applied to the medical material at the point of use, or in a pre-applied configuration. In certain embodiments, a pre-applied adhesive can be covered with release paper or similar material to protect the adhesive layer during shipping and handling. The release paper can then be removed prior to use.

Turning now to a discussion of the bolster material, any suitable biocompatible material can be used in the broader aspects of the invention. Reconstituted or naturally derived collagenous bolster materials are desirable, especially collagenous extracellular matrix materials, such as submucosa, renal capsule membrane, dura mater, pericardium, serosa, peritoneum, dermal collagen, or basement membrane. The preferred bolster materials of the invention will include submucosa, such as submucosa derived from a warm-blooded vertebrate. Mammalian submucosa materials retaining substantially their native cross-linking are preferred, although additionally crosslinked materials may also be used. In particular, extracellular matrix materials derived from animals raised for meat or other product production, e.g. pigs, cattle or sheep, will be advantageous. Porcine submucosa provides a particularly preferred material for use in the present invention.

The submucosa can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

When a submucosa or other ECM material having differing characteristic sides is used in the invention, it can be oriented upon the medical device with a specified side directed outward for contact with the arm(s) of the surgical fastening device. For example, in the case of small intestinal submucosa, the material may be oriented with either the luminal or abluminal side facing outwardly for contact with the arm(s) of the surgical fastening device.

As prepared, an extracellular matrix (ECM) material for use in the present invention may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein, or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206, 931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plate forming units (PFU) per gram, more preferably less than about 5 PFU per gram. These and additional properties of submucosa tissue taught in U.S. Pat. No. 6,206,931 may be characteristic of the ECM material used in the present invention.

Other implantable materials that may be employed as staple bolster materials in the present invention include non-bioresorbable or bioresorbable synthetic polymer materials such as polytetrofluroethylene (PTFE, e.g. GORE-TEX material), nylon, polypropylene, polyurethane, silicone, DACRON polymer, polyglycolic acid (PGA), polylactic acid (PLA), polycaprolactone, or others.

When a collagenous material is used as a staple bolster material in the invention, it may be desirable to bond areas of the collagenous material to one another, for example in securing the bolster material around all or a portion of an associated applicator element. Glues or other bonding agents may be used for this purpose, as discussed above. In addition or alternatively, collagenous material layers can be dehydrothermally bonded to one another, for example by drying the layers in contact with one another, e.g. under compression. The drying operation can, for example, occur in a lyophilization (freeze drying) or vacuum pressing process.

In certain embodiments of the invention, the staple bolster material will have a thickness in the range of about 50 to about 1000 microns, more preferably about 100 to 600 microns, and most preferably about 100 to about 350 microns. The staple bolster material will desirably provide sufficient strength to effectively reinforce the staple(s), for example exhibiting a suture retention strength in the range of about 100 to about 1000 gram force, e.g. typically in the range of about 200 to about 600 gram force, each of these based upon 5-0 Prolene suture and a bite depth of 2 mm. If necessary or desired, a multilaminate staple bolster material can be used. For example, a plurality of (i.e. two or more) layers of collagenous material, for example submucosa-containing or other ECM material, can be bonded together to form a multilaminate structure useful as a staple bolster material. Illustratively, two, three, four, five, six, seven, or eight or more collagenous layers containing submucosal or other collagenous ECM materials can be bonded together to provide a multilaminate collagenous bolster material. In certain embodiments, two to six collagenous, submucosa-containing layers isolated from intestinal tissue of a warm-blooded vertebrate, particularly small intestinal tissue, are bonded together to provide the staple bolster material. Porcine-derived small intestinal tissue is preferred for this purpose. The layers of collagenous tissue can be bonded together in any suitable fashion, including dehydrothermal bonding under heated, non-heated or lyophilization conditions, using adhesives, glues or other bonding agents, cross-linking with chemical agents or radiation (including UV radiation), or any combination of these with each other or other suitable methods.

The medical devices of the present invention can be used to facilitate a variety of surgical procedures. Such procedures include but are not limited to various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastro-intestinal procedures), and as a tool in a variety of other surgical procedures (e.g., reproductive organ repair procedures, etc.). In this regard, the medical devices of the invention may be used in conjunction with operations on both humans and animals. Likewise, the medical devices of the invention may be used with either anastomotic staplers or non-anastomotic staplers, and may be adapted, sized and shaped in a variety of ways to accommodate given stapler devices.

The medical devices of the invention can be provided in sterile packaging suitable for medical products. Sterilization may be achieved, for example, by irradiation, ethylene oxide gas, or any other suitable sterilization technique, and the materials and other properties of the medical packaging will be selected accordingly. In certain embodiments, the medical device is package in such a way so as to control the humidity within the sterile package. In some forms, the package includes a humidity control device, for example a device containing a desiccant such as a packet or card. In accordance with certain inventive variants, the sterile package includes a pocket configured to contain a humidity control device. In some forms, the medical packaging comprises a vapor impermeable material, for example a metallic foil (e.g. aluminum), or a polymeric material. In accordance with some forms, a vapor impermeable medical packaging may be utilized in conjunction with a radiation sterilization method as discussed herein. In certain embodiments, the medical packaging will be selected to maintain a desired humidity level within a sealed package containing a medical device as described herein. In accordance with certain embodiments, a medical product as described herein may be contained within an inner space of a sterile medical package. In some forms, the medical package is configured to maintain a humidity level of about 45% to about 75% relative humidity within the sealed medical package containing a medical device as described herein, preferably about 50% to about 65% relative humidity within the sealed medical package containing a medical device as described herein, even more preferably about 55% to about 60% relative humidity within the sealed medical package containing a medical device as described herein. In certain embodiment, the medical packaging is selected to maintain a relative humidity of about 58% within the sealed medical package containing a medical device as described herein.

Adhesive coatings as described herein may comprise a moisture content of about 2% to about 20%, preferably about 5% to about 15%, even more preferably about 10% to about 13%. In accordance with certain embodiments, the present disclosure provides a medical material comprising bolster material having an adhesive coating on at least a surface of the bolster material. In some forms, the medical material of the present disclosure comprises a moisture content of about 10% to about 35%, preferably about 15% to about 30%, even more preferably about 20% to about 25%.

Components of the medical adhesive described herein may be present in various relative amounts. For example, in some forms the present disclosure provides for a medical adhesive comprising a carboxymethyl cellulose and chondroitin sulfate at a dry weight ratio of 10:1 to 1:10, preferably 5:1 to 1:6, more preferably about 1:1. In some forms, the present disclosure provides a medical adhesive comprising chondroitin sulfate and sorbitol at a dry weight ratio of 1:1 to 1:20, preferably 1:5 to 1:15, more preferably about 1:10. In some forms, the present disclosure provides a medical adhesive comprising carboxymethyl cellulose and sorbitol at a dry weight ratio of 1:1 to 1:20, preferably 1:5 to 1:15, more preferably about 1:10. In some forms, the present disclosure provides for a medical adhesive comprising carboxymethyl cellulose, chondroitin sulfate, and sorbitol at a combination of the dry weight ratios described above. For example, in some forms a medical adhesive is provided comprising carboxymethyl cellulose, chondroitin sulfate, and sorbitol at a dry weight ratio of about 1:1:10.

In addition to the above components, in some forms a medical adhesive is provided also comprising maltitol and/ or sodium chloride. In some forms, the present disclosure provides a medical adhesive as described above and further comprising sorbitol and sodium chloride at a dry weight ratio of 10:1 to 1:1, preferably about 10:1.7. In some forms, the present disclosure provides a medical adhesive comprising sorbitol as described above, and maltitol at a dry weight ratio of 10:1 to 1:1, preferably about 10:3. It will be understood that any of the above described ratios may be combined to determine a ratio of relevant components. For example, in certain embodiments a medical adhesive is provided comprising chondroitin sulfate, carboxymethyl cellulose, sorbitol, maltitol, and sodium chloride at a dry weight ratio of about 1:1:10:3:1.7.

In accordance with certain embodiments, adhesive formulation may comprise water, for example high purity water. In some forms, an adhesive is provided comprising sorbitol at a level of 600 mg to 900 mg per ml of water, preferably about 750 mg per ml of water. In some forms, an adhesive is provided comprising maltitol at a level of 180 mg to 270 mg per ml of water, preferably about 225 mg per ml of water. In some forms, an adhesive is provided comprising sodium chloride at a level of 100 mg to 150 mg per ml of water, preferably about 125 mg per ml of water. In some forms, an adhesive is provided comprising chondroitin sulfate at a level of 60 mg to 90 mg per ml of water, preferably about 75 mg per ml of water. In some forms, an adhesive is provided comprising carboxymethyl cellulose at a level of 60 mg to 90 mg per ml of water, preferably about 75 mg per ml of water. It will be understood that any of the above described ranges may be combined. For example, in certain embodiments a medical adhesive is provided comprising about 75 mg chondroitin sulfate, about 75 mg carboxymethyl cellulose, about 750 mg sorbitol, about 225 mg maltitol, and about 125 mg sodium chloride per ml of water.

In certain embodiments, the present disclosure provides methods of preparing a medical product. In some forms, such methods comprise providing a medical material as first layer, and applying an adhesive to at least a portion of a surface of the medical material. The adhesive can be any adhesive as described herein. In accordance with some forms, a peelable protective cover as described herein may be applied over the adhesive. Certain methods may include packaging the medical material within a sterile and/or humidity controlled container or package.

As discussed herein the present disclosure provides medical adhesives having desirable adhesive strength. The medical adhesives described herein may have an average max load, performed according to ASTM 2256-05, of 2.5N to 6N, preferably 3 N to 5.5N, even more preferably 3.86N to 5.18N.

Turning now to a discussion of the illustrated embodiments, FIG. 1 illustrates one embodiment of a medial product 100 as presently disclosed. The illustrated embodiment comprises a medical graft material 102 and an adhesive 104. The illustrated embodiment comprises a first coated portion 106 and a second coated portion 108, such a configuration may be advantageous in a bolster material, for example to fit around a support material to facilitate loading of the material onto opposing faces of a surgical stapling device.

Figure 2A:
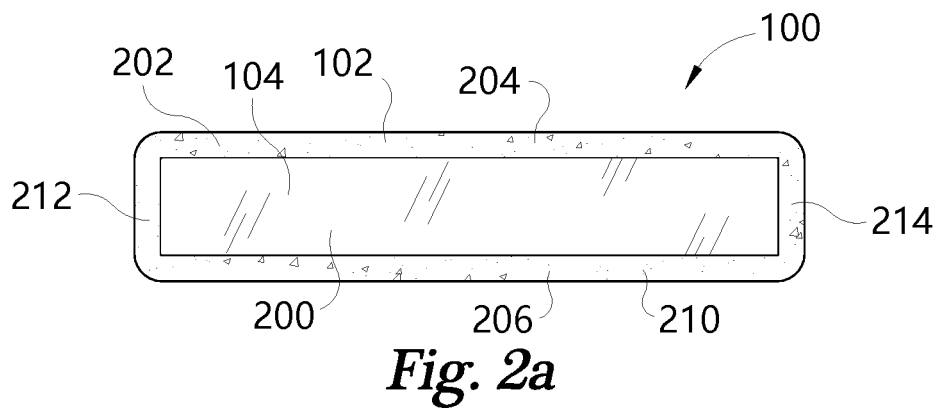
FIG. 2a is a top down view of one embodiment of a medical product as provided by the present disclosure.
Figure 2B:
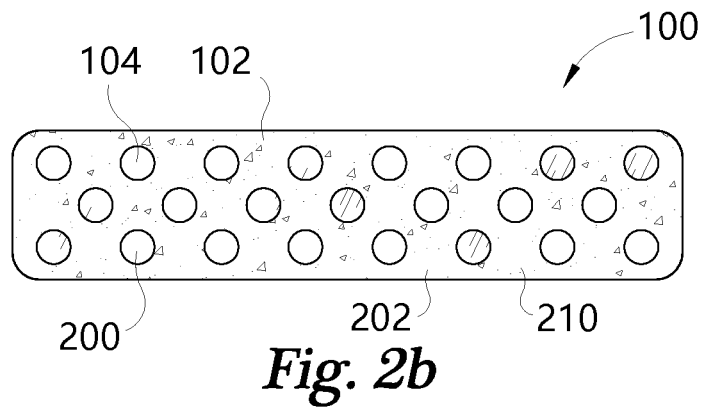
FIG. 2b is a top down view of one embodiment of a medical product as provided by the present disclosure.

FIGS. 2a and 2b show additional embodiments of medical products as disclosed herein. The illustrated embodiments include a medical product 100 comprising a medical graft material 102 and an adhesive 104. Medical products may include a surface 210 and one or more coated portions 200 and uncoated portions 202. Uncoated portions constitute portions of the surface which are free, or substantially free of adhesive. With reference to FIG. 2a, the illustrated embodiment includes uncoated lateral edges 204 and 206 and uncoated end edges 212 and 214. While the illustrated embodiment is shown with each of the edge portions uncoated by adhesive, it is within the scope of the disclosure to provide adhesive up to the edge of the graft material at one, two, thee, or four of the edges of the graft material. It is also within the scope of the disclosure to provide a coated portion extending around the periphery of a medical graft material while having one or more uncoated portions on the surface of the graft material bounded by coated portion(s). FIG. 2b illustrates an embodiment wherein the coated portion comprises a series of coated portions 200 on the surface of the medial graft material. In the illustrated embodiment the coated portions comprise a series of circular regions spaced on the graft surface. It is within the scope of this disclosure to provide coated regions having any suitable configuration, for example a coated portion may comprise one or more squares, rectangles, ovals, hexagons, or any other suitable shape.

Figure 3:
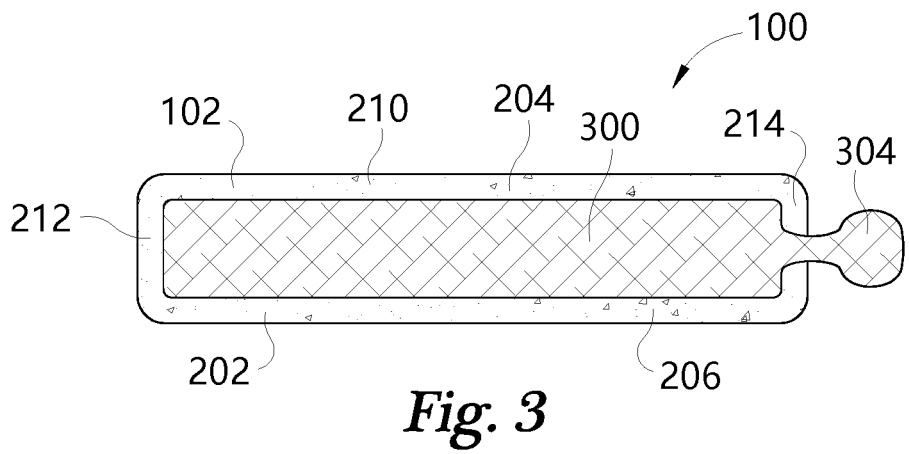
FIG. 3 is a top down view of one embodiment of a medical product as provided by the present disclosure.
Figure 4:
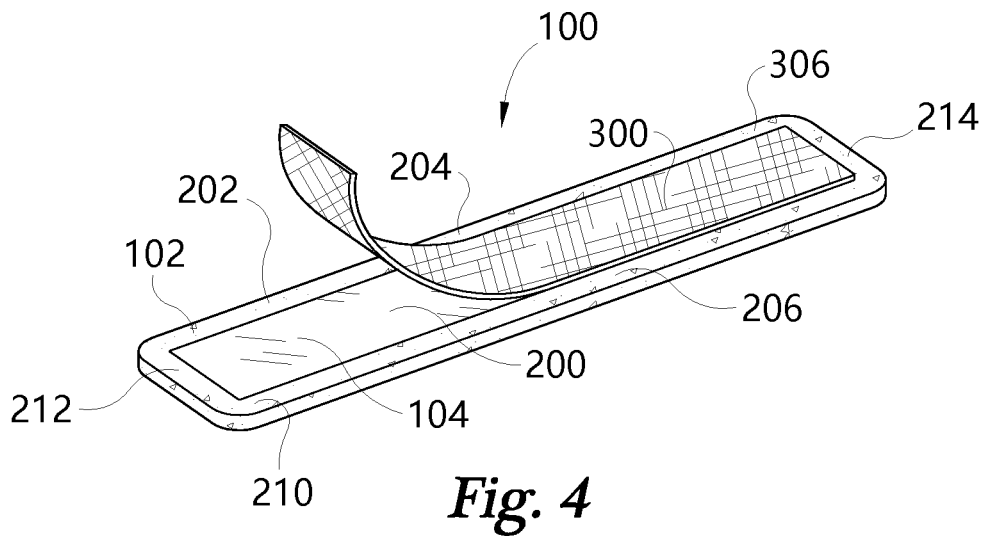
FIG. 4 is a perspective view of one embodiment of a medical product as provided by the present disclosure.

As detailed above, the present disclosure provides for medical products including a peelable protective cover. FIGS. 3 and 4 illustrate one embodiment of a medical product 100 as disclosed herein. In the illustrated embodiments, peelable protective cover 300 is positioned over the coated portion 200 on medical graft material 102. In the embodiment illustrated in FIG. 3, the peelable protective cover comprises attachment member 304. In some forms the attachment member is configured to secure the cover and/or medical product within a delivery tray. Attachment member may also be configured to facilitate peeling of the protective cover from the underlying adhesive. It is within the scope of the disclosure to provide a peelable protective cover covering all of the underlying medical graft material. In some forms the peelable protective cover is sized to cover the coated portion(s), leaving an uncovered portion 306 of the underlying medical graft material.

Figure 5A:
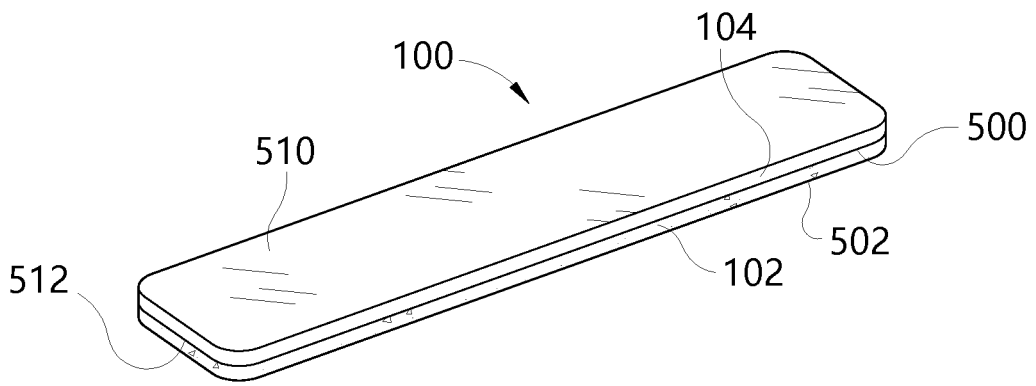
FIG. 5a is a perspective view of one embodiment of a medical product as provided by the present disclosure.
Figure 5B:
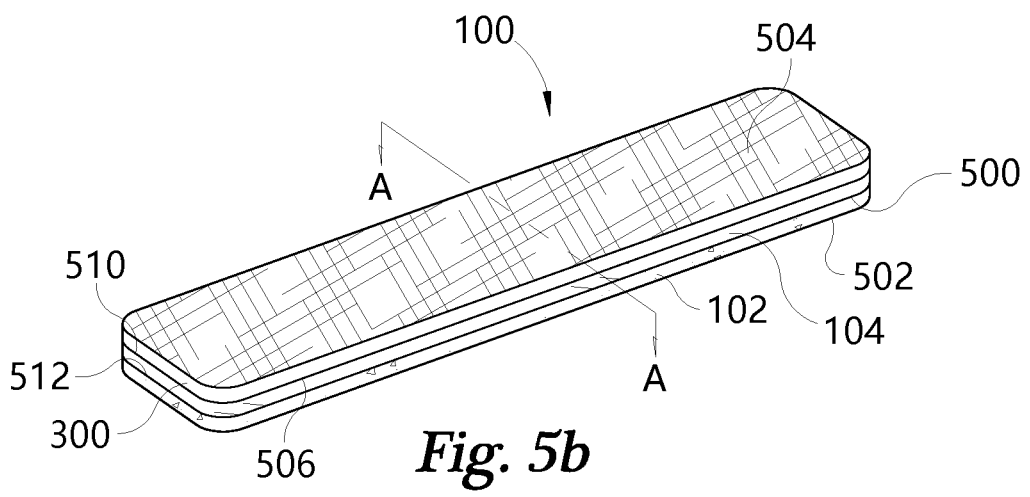
FIG. 5b is a perspective view of one embodiment of a medical product as provided by the present disclosure.
Figure 6:
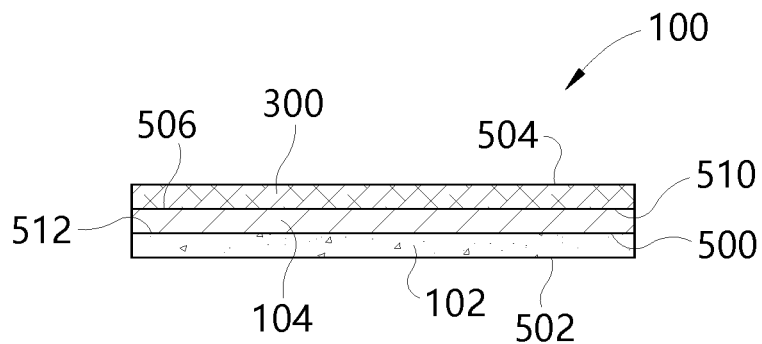
FIG. 6 is a cross-sectional view along line A of FIG. 5b.

Turning now to FIGS. 5a and 5b, shown are perspective views of exemplary embodiments of medical products as disclosed herein. The illustrated embodiments include a medical product 100 comprising a medical graft material 102. Medical graft material 102 has a first surface 500 and a second surface 502, in the illustrated embodiments adhesive 104 is present on the first surface while the second surface is uncoated. It is within the scope of the disclosure to provide a medical graft material having an adhesive coating on both the first and second surfaces. In the illustrated embodiment the adhesive covers substantially all of the first surface of the medical graft material. As shown, in some forms the adhesive layer has a first surface 510 configured for attachment to a medical device and/or patient tissue, the first surface may also be in contact with peelable protective cover 300. As shown in the illustrated embodiments, the adhesive layer may also include a second surface 512 in contact with the underlying medical graft material 102, for example the first surface 500 of the medical graft material. The embodiment illustrated in FIG. 5b includes a peelable protective cover 300 as disclosed herein. Peelable protective cover 300 has an outer surface 504, and a contact surface 506, wherein contact surface 506 is configured to contact the adhesive without adhering thereto. FIG. 6 is a cross-sectional view of the embodiment of FIG. 5b.

Figure 8:
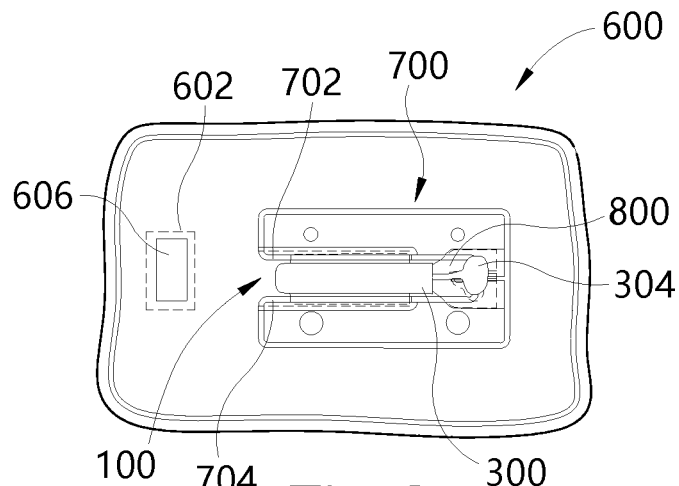
FIG. 8 is a top down view of one embodiment of a medical product as provided by the present disclosure.

With reference to FIG. 8, FIG. 8 illustrates one embodiment of a medical product as disclosed herein within a sterile medical package. In the illustrated embodiment, medical product 100 is packaged with a tray 700 and is contained within sterile package 600. Tray 700 may be configured to facilitate loading of the bolster material onto a surgical stapling device. For example, in some forms the tray may include side walls 702 and 704, configured to guide the jaws of a surgical stapling device to the bolster material. In certain embodiments, the tray may be configured to receive a support layer 800. In certain embodiments a support layer may comprise a rigid foam material and is configured to support the bolster material within the tray. Sterile package 600 includes pocket 602 configured to contain humidity control device 606. It is within the scope of the present disclosure to provide any of the embodiments of a medical device as disclosed herein, with or without a tray, within a sterile medical package.

While some discussions herein refer to carboxymethyl cellulose, in other embodiments, another carboxyalkyl cellulose (e.g. where the alkyl group has 2-5 carbon atoms, e.g. carboxymethyl or carboxypropyl cellulose), may be used in addition to or as an alternative to carboxymethyl cellulose.

The following specific Examples are provided to promote a further understanding of certain aspects of the present disclosure. It will be understood that these Examples are illustrative, and not limiting, in character.

Example 1

Preparation of Adhesive Composition

Adhesive compositions were prepared having the formulations listed in Table 1.

TABLE 1

Formulation details for adhesive compositions.

| Formulation ID | Components | Component Ratio |
|---|---|---|
| 1023A | CS:CMC:Sorbitol:HPW | 3:1:30:50 |
| 1023B | CS:CMC:Sorbitol:HPW | 3:1:30:33.3 |
| 1023C | CS:CMC:Sorbitol:HPW | 6:1:30:50 |
| 1023D | CS:CMC:Sorbitol:HPW | 3:1:50:50 |
| 1023E | CS:CMC:Sorbitol:HPW | 1:1:10:16.7 |
| 1023EG | CS:CMC:Glycerine:Sorbitol:HPW | 1:1:0.83:10:16.7 |
| 1023F | PASA:Sorbitol:HPW | 1:5:10 |
| 1023G | PAA:Sorbitol:HPW | 1:5:10 |
| 1023H | CS:CMC:Sorbitol:HPW | 3:1:15:35 |
| 1023I | CS:CMC:Sorbitol:HPW | 1:1:15:17.5 |
| 1023IG | CS:CMC:Sorbitol:Glycerine:HPW | 1:1:0.87:15:17.5 |
| Maltitol | CS:CMC:Sorbitol:Maltitol:NaCl:HPW | 1:1:10:3:1.7:13.3 |

Key:
CS—Chondroitin Sulfate, CMC—Carboxymethyl cellulose, HPW—High Purity Water, PASA—Poly(aspartic acid), PAA—Poly(acrylic acid)

Dry components of the adhesive compositions were weighed out, sifted together, and added to mixed liquid components (HPW or HPW and glycerin). Solutions were then dissolved on a shaker at 60 RPM for at least 4 hours.

Example 2

Preparation of Bolster Materials

Each of the formulations prepared according to Example 1 were coated onto 4-layer lyophilized SIS sheets using a 0.05 inch wire-wound rod. The coated sheets dried overnight at ambient humidity, then placed in a humidified container to equilibrate overnight. After equilibration, a release liner was applied to the coated surface of each sheet. Sheets were then laser cut to the desired shape using an Epilog laser cutter. Laser cut devices were packages in foil pouches with a 2-way humidifier packet (either 49% or 58%) to maintain humidity within the pouch. Some of the devices were sterilized with electron beam sterilization (dose: 26.0-39.3 kGy).

Example 3

Peel Strength

Peel testing was performed to compare the adhesive strength of several formulations. Preliminary qualitative testing was used to identify formulations that were qualitatively tacky and therefore suitable for peel testing. The results of the qualitative testing informed which formulations would be evaluated quantitatively by peel testing.

A peel test compared the adhesive strength of various formulation compositions. 4-layer SIS sheets were coated by the coating method described in Example 2 and allowed to equilibrate overnight in a humidified box. After equilibration, butcher paper was applied to the coated SIS and compressed with a 5 lb weight for at least 30 seconds and no more than 2 minutes. Coated SIS was peeled away from the applied sheet and the maximum tensile load and failure mode was measured and reported. This was performed according to ASTM 2256-05. Adhesive failure was preferred over cohesive failure because cohesive failure may result in residue buildup on stapler jaws.

In initial peel testing, formulations 1023E, 1023H, and 1023I were the most promising non-PAA formulations. They exhibited the highest peel strength after PAA and failed adhesively for most samples. Table 2 summarized the results.

TABLE 2

Summary of results from initial peel test for formulations comarision.

| Formulation ID | Avg. Max Load (N ± SD, n = 3) | Failure Mode |
|---|---|---|
| 1023A | 1.05 ± 0.18 | Cohesive |
| 1023B | 1.32 ± 0.23 | Cohesive |
| 1023C | 1.30 ± 0.43 | Cohesive |
| 1023D | 0.48 ± 0.11 | Cohesive |
| 1023E | 1.94 ± 0.40 | Adhesive |
| 1023F | 0.19 ± 0.06 | Cohesive |
| 1023G | 7.80 ± 1.20 | Adhesive |
| 1023H | 3.11 ± 1.03 | Adhesive/Some Residue |
| 1023I | 2.12 ± 0.37 | Adhesive/Some Residue |

Example 4

Peel Strength at Different Equilibrium Humidity Levels

A peel test evaluated the peel strength at different equilibrium humidity levels. Formulations 1023 E, 1023H, and 1023I were selected based on the results of Example 3. 4-layer SIS sheets were coated by the coating method described in Example 2 and allowed to equilibrate overnight to approximately 58%, 45%, or 38% relative humidity (RH). After equilibration, butcher paper was applied to the coated SIS and compressed with a 5 lb weight for at least 30 seconds and no more than 2 minutes. Coated SIS was peeled away from the applied sheet and the maximum tensile load and failure mode was measured and reported. This was performed according to ASTM 2256-05.

Samples equilibrated at 58% RH exhibited the highest peel strength. Table 3 summarizes the results.

TABLE 3

Summary of results from peel test for equilibrium humidity comparison

| Formulation ID | Equilibrium Humidity (% RH) | Avg. Max Load (N ± SD, n = 2) |
|---|---|---|
| 1023E | 58% | 4.52 ± 0.66 |
| 1023H | 58% | 5.20 ± 0.37 |
| 1023I | 58% | 5.54 ± 0.44 |
| 1023E | 45% | 3.81 ± 0.24 |
| 1023H | 45% | 2.92 ± 0.31 |
| 1023I | 45% | 4.80 ± 0.12 |
| 1023E | 38% | 4.27 ± 0.71 |
| 1023H | 38% | 3.07 ± 0.16 |
| 1023I | 38% | 4.20 ± 0.80 |

Example 5

Peel Strength of e-Beam Sterilized and Non-Sterilized Devices

A peel test compared e-beam sterilized and non-sterilized devices. E-beam sterilized devices were e-beam sterilized at a dose of 26.0-39.3 kGy. 4-layer SIS sheets were coated by the coating method described in Example 2 and allowed to equilibrate overnight to approximately 58% relative humidity (RH). After equilibration, 2-layer SIS was applied to the coated SIS and compressed with a 5 lb weight for at least 30 seconds and no more than 2 minutes. Coated SIS was peeled away from the applied sheet and the maximum tensile load and failure mode was measured and reported. This was performed according to ASTM 2256-05. Peel testing found that e-beam sterilization did not alter the failure mode or maximum peel strength. Table 4 summarizes the results.

TABLE 4

Summary of results from peel test comparing e-beam sterilized and non-sterile devices.

| Formulation ID | Equilibrium Humidity (% RH) | Avg. Max Load (N ± SD, n = 2) |
|---|---|---|
| 1023E-Sterilized | 58% | 2.54 ± 1.00 |
| 1023E-Non Sterile | 58% | 2.15 ± 0.87 |
| 1023IG-Sterilized | 58% | 1.09 ± 0.50 |
| 1023IG-Non Sterile | 58% | 0.96 ± 0.18 |

Example 6

Staple Performance Test

Stapler performance testing was conducted using SLR-coated devices with formulations selected based on peel testing detailed above. Formulations that exhibited both high pee strength and adhesive failure modes were subjected to stapler performance evaluations.

The first stapler test used SLR samples that were coated with adhesive and prepared by manually cutting the SLRA shape from a 4-layer SIS sheet, which was equilibrated at approximately 52% RH. Samples were loaded onto stapler jaws with Gripping Surface Technology (GST) or smooth cartridges. Samples were loaded without dipping the stapler or steaming the devices, and the stapler was fired into autoclave paper. The device was evaluated based on three criteria: device stapler adhesion, ease of SLR release from the stapler jaws after firing, and presence of adhesive residue remaining on the stapler surface. Formulation 1023E was selected due to its high peel strength and adhesive failure mode observed during peel testing. After the SLRA was applied to the stapler jaws (Ethicon) with a GST reload, the device remained in place and was easily released after firing into the autoclave paper without leaving stapler residue.

The second stapler performance test evaluated devices for adhesion to the stapler while manipulating porcine small intestine tissue heated to 37° C. The adhesive-coated devices were adhered to GST reloads, the stapler was fired, and ease of device deployment was assessed. Stapler surfaces were checked for adhesive residue after firing. Formulation 1023E was once again applied to the stapler jaws (Ethicon) with a GST reload. The device was hydrated by the porcine small intestinal tissue and remained in place throughout the test. The device was easily released from the stapler jaws after firing into the tissue and did not leave staple reside.

In the third stapler test, the formulations were subjected to additional porcine small intestine testing heated to 37° C. This time, the intestines were folded to be 2-3 times thicker than normal intestine. The goal was to challenge the device by moving and manipulating the surgical stapler. The surgical stapler was fired and devices were evaluated against the same evaluation criteria as the previous tests. For this tests formulations 1027A-1027I were coated onto SLP samples. The Ethicon Echelon stapler with GST reloads was used for each sample evaluation. After tissue the tissue was manipulated, moved, clamped, adjusted, unclamped, and fired, all samples remained adhered to the stapler jaws and were easily released after firing the stapler without residue.

In the fourth stapler test, e-beam sterilized devices were evaluated. Tissue was heated to 37° C. The selected formulations were coated on 4-layer sheets. All samples were loaded onto Ethicon Black GST type reloads using the Ethicon Echelon stapler. Samples were manually peeled off and re-adhered. The adhered devices were then slid around on the porcine stomach surface. As a worst-case test, samples were evaluated after being adhered, manipulating the tissue, and being set aside for approximately 10 min. After which, testing resumed and the stapler was fired into tissue. The adhesive was further challenges by being peeled off and then re-applied 2-3 times. The SLR device remained adhered and detached from the jaws after firing. during the test.

Example 7

Water Content Evaluation 4-layer SIS sheets were weighed at ambient conditions prior to coating, immediately after coating (wet), and after overnight equilibrium to determine the moisture content in the adhesive coating (n=3). Moisture content in the adhesive coating was calculated using the theoretical moisture content in the SIS (9%) as previously determined. All samples were coated with formulation 1023E using the method described in Example 2. Table 5 summarizes the results.

TABLE 5

Water content in samples after humidity equilibrium.

| Sample | Number of Specimens (n) | Equilibrium Humidity (% RH) | Moisture Content in Coating (% ± SD) | Moisture Content in Whole Sample (% ± SD) |
|---|---|---|---|---|
| 1 | 3 | 49 | 6.1 ± 2.2 | 20.4 ± 2.3 |
| 2 | 3 | 58 | 11.5 ± 1.5 | 23.0 ± 1.8 |

Example 8

An adhesive formulation as described above was prepared; further comprising maltitol and sodium chloride to inhibit crystallization. The adhesive was prepared as shown in Table 6 below.

TABLE 6

| Adhesive formulation (v3). | |
|---|---|
| Sorbitol | 24 g |
| Maltitol | 7.2 g |
| NaCl | 4 g |
| Chondroitin Sulfate | 2.4 g |
| Carboxymethylcellulose | 2.4 g |
| High Purity Water | 32 g |

Figure 7:
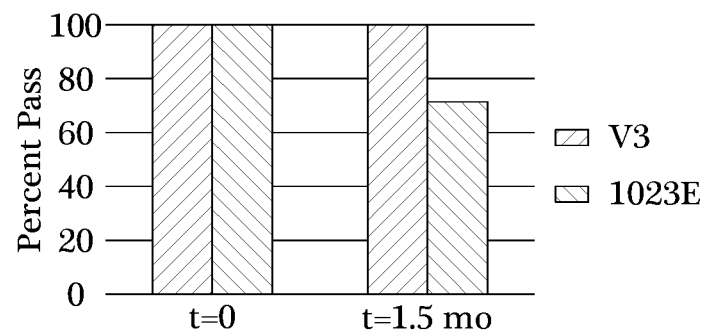
FIG. 7 is a graph detailing the results of the analysis discussed at Example 8.

The above formulation was tested for stapler adhesion immediately after formulation, and after aging for 1.5 months. A comparative analysis was performed to determine stapler adhesion during aging. Stapler adhesion was determined at t=0 (immediately after application to a bolster material) and at t=1.5 mo (1.5 months after application to bolster material), using formulation 1023E described above and the modified formulation (v3) of Table 6. The results of the analysis are shown in FIG. 7. The addition of crystallization inhibitors did not affect staple adhesion at t=0, and improved staple adhesion at t=1.5 months.

Listing of Certain Embodiments

The following provides an enumerated listing of some of the embodiments disclosed herein. It will be understood that this listing is non-limiting, and that individual features or combinations of features (e.g. 2, 3 or 4 features) as described in the Detailed Description above can be incorporated with the below-listed Embodiments to provide additional disclosed embodiments herein.

1. A medical product, comprising:
   a medical graft material; and
   an adhesive on at least a portion of a surface of said medical graft material, wherein said adhesive comprises: a carboxyalkyl cellulose, and sorbitol.
2. The medical product of embodiment 1, wherein said carboxyalkyl cellulose is carboxymethyl cellulose.
3. The medical product of any one of the preceding embodiments, wherein said adhesive further comprises a sulfated glycosaminoglycan.
4. The medical product of embodiment 3, wherein said sulfated glycosaminoglycan comprises chondroitin sulfate.
5. The medical product of embodiment 4, wherein said carboxyalkyl cellulose is carboxymethyl cellulose, and wherein said carboxymethyl cellulose and said chondroitin sulfate are present in a ratio of 10:1 to 1:3.
6. The medical product of any one of the preceding embodiments, wherein said adhesive further comprises maltitol.
7. The medical product of embodiments 6, wherein said sorbitol and said maltitol are present in a ratio of 10:1 to 1:1.
8. The medical product of embodiment 7, wherein said sorbitol and said maltitol are present in a ratio of about 10:3.
9. The medical product of any one of the preceding embodiments, wherein said adhesive further comprises sodium chloride.
10. The medical product of embodiment 9, wherein said sorbitol and said sodium chloride are present in a ratio of 10:1 to 1:1.
11. The medical product of embodiment 10, wherein said sorbitol and said sodium chloride are present in a ratio of about 10:1.7.
12. The medical product of any one of the preceding embodiments, further comprising a peelable protective cover over said adhesive.
13. The medical product of any one of the preceding embodiments, wherein said medical graft material is contained within a sterile package.
14. The medical product of embodiment 13, wherein said medical graft material is contained within an inner space of said sterile package, and wherein said sterile package is configured to maintain the inner space at a humidity level of 50-65% relative humidity.
15. The medical product of any one of the preceding embodiments, wherein said medical graft material comprises a biological material.
16. The medical product of embodiment 15, wherein said biological material comprises an extracellular matrix material.
17. The medical product of embodiment 16, wherein said extracellular matrix material comprises submucosa, renal capsule membrane, dura mater, pericardium, serosa, peritoneum, dermal collagen, or basement membrane
18. The medical product of any one of the preceding embodiments, wherein said medical graft material comprises a bolster material configured for application to an arm of a surgical fastening device.
19. The medical product of any one of the preceding embodiments, wherein said portion comprises at least 80% of said surface.
20. The medical product of any one of the preceding embodiments, wherein said adhesive has a moisture content of 5% to 15%.
21. The medical product of any one of the preceding claims, wherein said adhesive has an adhesive strength of 2.5 N to 6 N.
22. A medical adhesive comprising:
   a carboxyalkyl cellulose, sorbitol, maltitol, a sulfated glycosaminoglycan, and a salt.
23. The medical adhesive of embodiment 22, wherein said carboxyalkyl cellulose is carboxymethyl cellulose.
24. The medical adhesive of embodiment 22, wherein said sulfated glycosaminoglycan comprises chondroitin sulfate.
25. The medical adhesive of embodiment 24, wherein said carboxyalkyl cellulose is carboxymethyl cellulose, and wherein said carboxymethyl cellulose and said chondroitin sulfate are present in a dry weight ratio of 10:1 to 1:3.
26. The medical adhesive of embodiment 22, wherein said sorbitol and said maltitol are present in a dry weight ratio of 10:1 to 1:1.
27. The medical adhesive of embodiment 26, wherein said sorbitol and said maltitol are present in a dry weight ratio of about 10:3.
28. The medical adhesive of any one of embodiments 22 to 27, wherein said salt comprises sodium chloride.
29. The medical adhesive of embodiment 28, wherein said sorbitol and said sodium chloride are present in a dry weight ratio of 10:1 to 1:1.
30. The medical adhesive of embodiment 29, wherein said sorbitol and said sodium chloride are present in a dry weight ratio of about 10:1.7.
31. The medical adhesive of embodiment 22, wherein said a carboxyalkyl cellulose comprises carboxymethyl cellulose, said sulfated glycosaminoglycan comprises chondroitin sulfate, and said salt comprises sodium chloride, and wherein said chondroitin sulfate, said carboxymethyl cellulose, said sorbitol, said maltitol, and said sodium chloride are present in a dry weight ratio of 1:1:10:3:1.7.

32. The medical adhesive of any one of embodiments 22 to 31, wherein said adhesive has a moisture content of 5% to 15%.

33. The medical adhesive of any one of embodiments 22 to 32, wherein said adhesive forms a coating on at least a portion of a surface of a medical graft material.

34. The medical adhesive of embodiment 33, further comprising a peelable protective cover over said coating.

35. The medical adhesive of any one of embodiments 33 or 34 wherein said medical graft material comprises a collagenous extracellular matrix material.

36. The medical adhesive of embodiment 35, wherein said collagenous extracellular matrix material comprises submucosa, renal capsule membrane, dura mater, pericardium, serosa, peritoneum, dermal collagen, or basement membrane.

37. A method for preparing a medical product, comprising:
providing a medical material as a first layer;
applying an adhesive to at least a portion of a surface of the medical material, the adhesive comprising a carboxyalkyl cellulose and sorbitol;
applying a peelable protective cover to the adhesive, said peelable protective cover peelable to expose the adhesive on the medical material.

38. The method of embodiment 37 wherein the carboxyalkyl cellulose is carboxymethyl cellulose.

39. The method of any one of embodiments 37 or 38, wherein the adhesive further comprises a sulfated glycosaminoglycan.

40. The method of embodiment 39, wherein the sulfated glycosaminoglycan comprises chondroitin sulfate.

41. The method of embodiment 40, wherein the carboxyalkyl cellulose is carboxymethyl cellulose, and wherein the carboxymethyl cellulose and the chondroitin sulfate are present in a ratio of 10:1 to 1:3.

42. The method of any one of embodiments 37 to 41, wherein the adhesive further comprises maltitol.

43. The method of embodiment 42, wherein the sorbitol and the maltitol are present in a ratio of 10:1 to 1:1.

44. The method of embodiment 43, wherein the sorbitol and the maltitol are present in a ratio of about 10:3.

45. The method of any one of embodiments 37 to 44, wherein the adhesive further comprises sodium chloride.

46. The method of embodiment 45, wherein the sorbitol and the sodium chloride are present in a ratio of 10:1 to 1:1.

47. The method of embodiment 46, wherein the sorbitol and the sodium chloride are present in a ratio of about 10:1.7.

48. The method of any one of embodiments 37 to 48, packaging the medical product within a sterile package.

49. The method of embodiment 48, wherein the medical product is contained within an inner space of the sterile package, and wherein the sterile package is configured to maintain the inner space at a humidity level of 50-65% relative humidity.

50. The method of any one of embodiments 37 to 49, wherein the medical material comprises a biological material.

51. The method of embodiment 50, wherein the biological material comprises an extracellular matrix material.

52. The method of embodiment 51, wherein the extracellular matrix material comprises submucosa, renal capsule membrane, dura mater, pericardium, serosa, peritoneum, dermal collagen, or basement membrane.

53. The method of any one of embodiments 37 to 52, wherein said medical graft material comprises a bolster material configured for application to an arm of a surgical fastening device.

54. The method of any one of embodiments 37 to 53, wherein said applying an adhesive is conducted to create a coated portions portion comprises at least 80% of the surface of the medical material.

55. A bolster material configured for application to an arm of a surgical fastening device, said bolster material comprising:
an adhesive coating on at least a portion of a surface of said bolster material, wherein said adhesive coating comprises a carboxyalkyl cellulose, and sorbitol.

56. The bolster material of embodiment 55, wherein said carboxyalkyl cellulose is carboxymethyl cellulose.

57. The bolster material of any one of embodiments 55 or 56, wherein said adhesive coating further comprising a sulfated glycosaminoglycan.

58. The bolster material of embodiment 57, wherein said sulfated glycosaminoglycan comprises chondroitin sulfate.

59. The bolster material of embodiment 58, wherein said carboxyalkyl cellulose is carboxymethyl cellulose, and wherein said carboxymethyl cellulose and said chondroitin sulfate are present in a ratio of 10:1 to 1:3.

60. The bolster material of any one of embodiments 55 to 59, wherein said adhesive coating further comprising maltitol.

61. The bolster material of embodiment 60, wherein said sorbitol and said maltitol are present in a ratio of 10:1 to 1:1.

62. The bolster material of embodiment 61, wherein said sorbitol and said maltitol are present in a ratio of about 10:3.

63. The bolster material of any one of embodiments 55 to 62, wherein said adhesive coating further comprising sodium chloride.

64. The bolster material of embodiment 63, wherein said sorbitol and said sodium chloride are present in a ratio of 10:1 to 1:1.

65. The bolster material of embodiment 64, wherein said sorbitol and said sodium chloride are present in a ratio of about 10:1.7.

66. The bolster material of any one of embodiments 55 to 65, further comprising a peelable protective cover over said adhesive coating.

67. The bolster material of any one of embodiments 55 to 66, wherein said bolster material is contained within a sterile package.

68. The bolster material of embodiment 67, wherein said bolster material is contained within an inner space of said sterile package, and wherein said sterile package is configured to maintain the inner space at a humidity level of 50-65% relative humidity.

69. The bolster material of any one of embodiments 55 to 68, wherein the bolster material comprises a collagenous extracellular matrix material.

70. The bolster material of embodiment 69, wherein said collagenous extracellular matrix material comprises submucosa, renal capsule membrane, dura mater, pericardium, serosa, peritoneum, dermal collagen, or basement membrane.

71. The bolster material of any one of embodiments 55 to 70, wherein said portion comprises at least 80% of said surface.

72. The bolster material of any one of embodiments 55-71, wherein said bolster material is received within a loading tray configured to facilitate application of the bolster material to an arm of a surgical fastening device.

73. A method for loading a bolster material on a surgical fastening device, comprising:

providing a bolster material configured for application to a working surface of the surgical fastening device, the bolster material having an adhesive coating on at least a portion of a surface of said bolster material, the adhesive coating comprising a carboxyalkyl cellulose and sorbitol; and contacting said adhesive material against the working surface of the surgical fastening device so as to adhere the bolster material to the working surface.

74. The method of embodiment 73, wherein the carboxyalkyl cellulose is carboxymethyl cellulose.

75. The method of any one of embodiments 73 or 74, wherein the adhesive further comprises a sulfated glycosaminoglycan.

76. The method of embodiment 75, wherein the sulfated glycosaminoglycan comprises chondroitin sulfate.

77. The method of embodiment 76, wherein the carboxyalkyl cellulose is carboxymethyl cellulose, and wherein the carboxymethyl cellulose and the chondroitin sulfate are present in a dry weight ratio of 10:1 to 1:3.

78. The method of any one of embodiments 73 to 77, wherein the adhesive further comprises maltitol.

79. The method of embodiment 78, wherein the sorbitol and the maltitol are present in a dry weight ratio of 10:1 to 1:1.

80. The method of embodiment 79, wherein said sorbitol and said maltitol are present in a dry weight ratio of about 10:3.

81. The method of any one of embodiments 73 to 80, wherein the adhesive further comprises sodium chloride.

82. The method of embodiment 81, wherein the sorbitol and the sodium chloride are present in a dry weight ratio of 10:1 to 1:1.

83. The method of embodiment 82, wherein the sorbitol and the sodium chloride are present in a dry weight ratio of about 10:1.7.

84. The method of any one of embodiments 73 to 83, wherein the medical graft material comprises a biological material.

85. The method of embodiment 84, wherein the biological material comprises an extracellular matrix material.

86. The method of embodiment 85, wherein the extracellular matrix material comprises submucosa, renal capsule membrane, dura mater, pericardium, serosa, peritoneum, dermal collagen, or basement membrane.

87. The method of any one of embodiments 73 to 86, wherein the portion comprises at least 80% of the surface.

88. The method of any one of embodiments 73 to 87, wherein the adhesive has a moisture content of 5% to 15%.

89. A medical product, comprising:

a medical graft material; and an adhesive on at least a portion of a surface of said medical graft material, wherein said adhesive comprises a carboxyalkyl cellulose, a sugar alcohol, and at least one of a crystallization inhibiting salt and a sulfated glycosaminoglycan.

90. The medical product of embodiment 89, wherein said adhesive comprises a sulfated glycosaminoglycan.

91. The medical product of embodiment 89, wherein said carboxyalkyl cellulose comprises carboxymethyl cellulose and/or wherein said adhesive comprises both a crystallization inhibiting salt and a sulfated glycosaminoglycan.

92. The medical product of any one of embodiments 90 or 91, wherein said sulfated glycosaminoglycan comprises chondroitin sulfate.

93. The medical product of embodiment 92, wherein said carboxyalkyl cellulose and said chondroitin sulfate are present in a dry weight ratio of 10:1 to 1:3.

94. The medical product of any one of embodiments 89 to 93, wherein said adhesive comprises sorbitol and maltitol.

95. The medical product of embodiment 94, wherein said sorbitol and said maltitol are present in a dry weight ratio of 10:1 to 1:1.

96. The medical product of embodiment 95, wherein said sorbitol and said maltitol are present in a dry weight ratio of about 10:3.

97. The medical product of any one of embodiments 89 to 96, wherein said crystallization inhibiting salt comprises sodium chloride.

98. The medical product of embodiment 97, wherein said adhesive comprises sorbitol and sodium chloride in a dry weight ratio of 10:1 to 1:1.

99. The medical product of embodiment 98, wherein said sorbitol and said sodium chloride are present in a dry weight ratio of about 10:1.7.

100. The medical product of any one of embodiments 89 to 99, further comprising a peelable protective cover over said adhesive.

101. The medical product of any one of embodiments 89 to 100, wherein said medical graft material is contained within a sterile package.

102. The medical product of embodiment 101, wherein said medical graft material is contained within an inner space of said sterile package, and wherein said sterile package is configured to maintain the inner space at a humidity level of about 50 to about 65% relative humidity.

103. The medical product of any one of embodiments 89 to 102, wherein said medical graft material comprises a biological material.

104. The medical product of embodiment 103, wherein said biological material comprises an extracellular matrix material.

105. The medical product of embodiment 104, wherein said extracellular matrix material comprises submucosa, renal capsule membrane, dura mater, pericardium, serosa, peritoneum, dermal collagen, or basement membrane.

106. The medical product of any one of embodiments 89 to 105, wherein said medical graft material comprises a bolster material configured for application to an arm of a surgical fastening device.

107. The medical product of any one of embodiments 89 to 106, wherein said portion comprises at least 80% of said surface.

108. The medical product of any one of embodiments 89 to 107, wherein said adhesive has a moisture content of 5% to 15%.

109. The medical product of any one of embodiments 89 to 108, wherein said adhesive has an adhesive strength of 2.5 N to 6 N.

110. A medical adhesive comprising:

a carboxyalkyl cellulose, a sugar alcohol, and at least one of a sulfated glycosaminoglycan and a crystallization inhibiting salt.

111. The medical adhesive of embodiment 110, wherein said carboxyalkyl cellulose comprises carboxymethyl cellulose.

112. The medical adhesive of embodiment 110, wherein said sulfated glycosaminoglycan comprises chondroitin sulfate.

113. The medical adhesive of embodiment 112, wherein said carboxyalkyl cellulose and said chondroitin sulfate are present in a dry weight ratio of 10:1 to 1:3.

114. The medical adhesive of embodiment 110, comprising sorbitol and maltitol in a dry weight ratio of 10:1 to 1:1.

115. The medical adhesive of embodiment 114, wherein said sorbitol and said maltitol are present in a dry weight ratio of about 10:3.

116. The medical adhesive of any one of embodiments 110 to 115, wherein said crystallization inhibiting salt comprises sodium chloride.

117. The medical adhesive of embodiment 116, comprising sorbitol and said sodium chloride in a dry weight ratio of 10:1 to 1:1.

118. The medical adhesive of embodiment 117, wherein said sorbitol and said sodium chloride are present in a dry weight ratio of about 10:1.7.

119. The medical adhesive of embodiment 110, wherein said a carboxyalkyl cellulose comprises carboxymethyl cellulose, said sulfated glycosaminoglycan comprises chondroitin sulfate, and said crystallization inhibiting salt comprises sodium chloride.

120. The medical adhesive of any one of embodiments 110 to 119, wherein said adhesive has a moisture content of 5% to 15%.

121. The medical adhesive of any one of embodiments 110 to 120, wherein said adhesive forms a coating on at least a portion of a surface of a medical graft material.

122. The medical adhesive of embodiment 121, further comprising a peelable protective cover over said coating.

123. The medical adhesive of any one of embodiments 121 or 122 wherein said medical graft material comprises a collagenous extracellular matrix material.

124. The medical adhesive of embodiment 123, wherein said collagenous extracellular matrix material comprises submucosa, renal capsule membrane, dura mater, pericardium, serosa, peritoneum, dermal collagen, or basement membrane.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical product, comprising:
 a medical graft material; and
 an adhesive on at least a portion of a surface of said medical graft material, wherein said adhesive comprises: chondroitin sulfate, carboxymethyl cellulose, sorbitol, and maltitol.

2. The medical product of claim 1, wherein said carboxyalkyl cellulose is carboxymethyl cellulose, and wherein said carboxymethyl cellulose and said chondroitin sulfate are present in a dry weight ratio of 10:1 to 1:3.

3. The medical product of claim 1, wherein said sorbitol and said maltitol are present in a dry weight ratio of 10:1 to 1:1.

4. The medical product of claim 1, wherein said adhesive further comprises sodium chloride, and wherein said sorbitol and said sodium chloride are present in a dry weight ratio of 10:1 to 1:1.

5. The medical product of claim 1, wherein said medical graft material is contained within an inner space of a sterile package, and wherein said sterile package is configured to maintain the inner space at a humidity level of 50-65% relative humidity.

6. A medical adhesive comprising:
 a carboxyalkyl cellulose, sorbitol, maltitol, a sulfated glycosaminoglycan, and a salt.

7. The medical adhesive of claim 6, wherein said sorbitol and said maltitol are present in a dry weight ratio of 10:1 to 1:1.

8. The medical adhesive of claim 6, wherein said a carboxyalkyl cellulose comprises carboxymethyl cellulose, said sulfated glycosaminoglycan comprises chondroitin sulfate, and said salt comprises sodium chloride, and wherein said chondroitin sulfate, said carboxymethyl cellulose, said sorbitol, said maltitol, and said sodium chloride are present in a dry weight ratio of 1:1:10:3:1.7.

9. The medical adhesive of claim 6, wherein said adhesive has a moisture content of 5% to 15%.

10. A medical adhesive comprising:
 a carboxyalkyl cellulose, a sugar alcohol, and at least one of a sulfated glycosaminoglycan and a crystallization inhibiting salt.

11. The medical adhesive of claim 10, wherein said carboxyalkyl cellulose comprises carboxymethyl cellulose, wherein said sulfated glycosaminoglycan comprises chondroitin sulfate, and wherein said carboxymethyl cellulose and said chondroitin sulfate are present in a dry weight ratio of 10:1 to 1:3.

12. The medical adhesive of claim 10, comprising sorbitol and maltitol in a dry weight ratio of 10:1 to 1:1.

13. The medical adhesive of claim 10, wherein said crystallization inhibiting salt comprises sodium chloride, and said sugar alcohol comprises sorbitol, and wherein said sorbitol and said sodium chloride are present in the adhesive in a dry weight ratio of 10:1 to 1:1.

14. The medical adhesive of claim 13, comprising sorbitol and said sodium chloride in a dry weight ratio of 10:1 to 1:1.

* * * * *